United States Patent
Zhang

(10) Patent No.: US 11,958,808 B2
(45) Date of Patent: Apr. 16, 2024

(54) ACETYLSALICYLIC ACID DERIVATIVE AND APPLICATION THEREOF

(71) Applicant: Zhejiang Hanmai Pharmaceutical Technology Co., Ltd., Shaoxing (CN)

(72) Inventor: Jing Zhang, Shanghai (CN)

(73) Assignee: ZHEJIANG HANMAI PHARMACEUTICAL TECHNOLOGY CO., LTD., Shaoxing (CN)

( * ) Notice: Subject to any disclaimer, the term of this patent is extended or adjusted under 35 U.S.C. 154(b) by 156 days.

(21) Appl. No.: 17/419,448

(22) PCT Filed: Dec. 26, 2019

(86) PCT No.: PCT/CN2019/128617
§ 371 (c)(1),
(2) Date: Jun. 29, 2021

(87) PCT Pub. No.: WO2020/135560
PCT Pub. Date: Jul. 2, 2020

(65) Prior Publication Data
US 2021/0387950 A1 Dec. 16, 2021

(30) Foreign Application Priority Data

Dec. 29, 2018 (CN) .......................... 201811653721.7

(51) Int. Cl.
C07D 211/16 (2006.01)
C07C 235/78 (2006.01)
C07D 203/18 (2006.01)

(52) U.S. Cl.
CPC .......... C07D 211/16 (2013.01); C07C 235/78 (2013.01); C07D 203/18 (2013.01); C07B 2200/13 (2013.01)

(58) Field of Classification Search
CPC ............... C07D 211/16; C07D 203/18; C07D 295/185; C07C 235/78; C07C 235/06; C07B 2200/13; A61P 29/00
(Continued)

(56) References Cited

U.S. PATENT DOCUMENTS 5,073,641 A 12/1991 Bundgaard et al.

FOREIGN PATENT DOCUMENTS

| CN | 101484415 A | 7/2009 |
| CN | 101484415 B | 8/2013 |

(Continued)

OTHER PUBLICATIONS

Osman et al al , Synthesis and biological activity of salicylic acid esters Journal de Pharmacie de Belgique, 1984, 39(5), p. 280-284 (abstract—2 pages) (Year: 1984).*

(Continued)

*Primary Examiner* — Taylor V Oh
(74) *Attorney, Agent, or Firm* — HSML P.C.

(57) ABSTRACT

An acetylsalicylic acid derivative and an application thereof. The present disclosure relates to the field of chemical pharmaceuticals, and in particular, to a compound shown in formula (I) or pharmaceutically acceptable salts thereof.

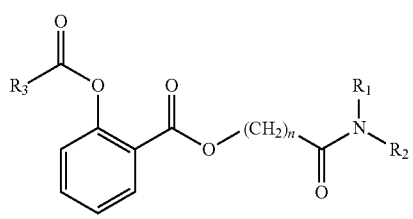

(I)

25 Claims, 2 Drawing Sheets

(58) Field of Classification Search
USPC .......................................................... 546/226
See application file for complete search history.

(56) References Cited

FOREIGN PATENT DOCUMENTS

| GB | 1379009 | | 1/1975 |
|---|---|---|---|
| JP | S4966645 | A | 6/1974 |
| JP | H01501310 | A | 5/1989 |
| JP | 2009542797 | A | 12/2009 |
| WO | 8801615 | A1 | 3/1988 |
| WO | 2008007171 | | 1/2008 |

OTHER PUBLICATIONS

Extended European Search Report issued for European Patent Application No. 19901822.7, dated Aug. 11, 2022, 6 pages.
Nielsen, N. M. et al., "Evaluation of Glycolamide Esters and Various Other Esters of Aspirin as True Aspirin Prodrugs," Journal of Medicinal Chemistry, vol. 32, No. 3, 1989, pp. 727-734. Cited in PCT International Search Report.
International Search Report issued for International Patent Application No. PCT/CN2019/128617, dated Mar. 30, 2020, 5 pages including English translation.
First Office Action issued for Chinese Patent Application No. 201980079507.1, dated Aug. 8, 2023, 14 pages including English translation.
Communication pursuant to Article 94(3) EPC issued for European Patent Application No. 19901822.7, dated Oct. 9, 2023, 4 pages.
Moerk Nielsen, N. et al., "Evaluation of Glycolamide Esters and Various Other Esters of Aspirin as True Aspirin Prodrugs," Journal of Medicinal Chemistry, 1989, vol. 32, No. 3, pp. 727-734. (Cited in JP Office Action).
Gilmer, J. F. et al., "Evaluation of nitrate-substituted pseudocholine esters of aspirin as potential nitro-aspirins," Bioorganic & Medicinal Chemistry Letters, 2007, vol. 17, No. 11, pp. 3217-3220. (Cited in JP Office Action).
Amir, M. et al., "Synthesis and antiinflammatory activity of some new glycolamide esters of arylalkanoic acids," Indian Journal of Heterocyclic Chemistry, 2001, vol. 10, pp. 181-184. (Cited in JP Office Action).
Kazuhide Ashizawa, "Polymorphic Phenomena of Pharmaceuticals and Chemistry of Crystallization," 2002, pp. 273, 278, 305-317. (Relevance discussed in English translation of JP Office Action cited below).
Moriarty, L.M. et al., "Discovery of a "True" Aspirin Prodrug," Journal of Medicinal Chemistry, 2008, vol. 51, No. 24, pp. 7991-7999. (Cited in JP Office Action).
Notice of Reasons for Refusal issued for Japanese Patent Application No. 2021-538409, Dispatch Date: Dec. 19, 2023, 14 pages including English machine translation.

* cited by examiner

ACETYLSALICYLIC ACID DERIVATIVE AND APPLICATION THEREOF

TECHNICAL FIELD

The present disclosure relates to the field of chemical pharmaceuticals, in particular to an acetylsalicylic acid derivative and its application.

BACKGROUND ART

As early as in 1853, Charles Frederic Gerhardt synthesized acetylsalicylic acid from salicylic acid and acetic anhydride, but it failed to attract people's attention. In 1897, Felix Hoffman, a German chemist, synthesized acetylsalicylic acid again, and used it to treat his father's rheumatoid arthritis with excellent results. In 1899, Dreser introduced it to clinical treatment and named it aspirin. Having been used for more than one hundred years, aspirin has become one of the three most classic drugs in the history of medicine. So far, it is still the most widely used antipyretic, analgesic and anti-inflammatory drug in the world. It's also a standard formulation for comparison to evaluate other drugs. It has an antithrombotic effect in vivo. It can inhibit aggregation of platelets and reduce the risk of thrombosis. It is widely used by patients with cardiovascular diseases, especially coronary heart disease, cerebral infarction and thrombotic lesions. The curative effect is definite.

Gastrointestinal symptoms are the most common side effects of aspirin. The common symptoms include nausea, vomiting, epigastric discomfort or pain, etc. Oral administration of aspirin may directly stimulate the gastric mucosa and cause epigastric discomfort, nausea and vomiting. Long-term administration tends to cause gastric mucosal lesion, gastric ulcer and gastric bleeding. Therefore, in the case of long-term oral administration of aspirin, hemogram monitoring, fecal occult blood testing and necessary gastroscopy should be applied regularly.

In addition, many people have misconceptions about the usage and timing of aspirin administration. Since the advent of aspirin enteric-coated tablets, the harm of this drug to gastric mucosa has often been ignored. Some physicians believe that if the dose taken is very small, there will be no harm to gastric mucosa despite long-term administration of aspirin. However, in fact, the situation is not that simple. Many patients do experience adverse drug reactions in the end. The pharmacological mechanism of enteric-coated aspirin is as follows: the use of an acid-resistant coating of the outer layer of a tablet prevents it from disintegrating in the acidic environment of stomach; instead, only when it enters the weakly alkaline intestinal juice in intestine, it's disintegrated and absorbed to exert the effect of aspirin. However, if the stomach contents are weakly alkaline, there will be no guarantee that an aspirin enteric-coated tablet will not disintegrate, considering that people's dietary habits and structures are not exactly the same. Even if the disintegration and absorption of aspirin is exclusively completed in the intestine, it may also have a stimulating effect on the intestine.

Chinese Patent CN 101484415 B discloses an aspirin prodrug (an acetylsalicylic acid derivative). This prodrug can enter the body via transdermal administration. It has the effects of its corresponding original drug (aspirin) as a non-steroidal anti-inflammatory drug, but avoids gastrointestinal adverse reactions caused by oral administration of common non-steroidal anti-inflammatory drugs. The molecule of this aspirin prodrug comprises two ester bonds, one of which (an acetyl group) originates from salicylic acid itself, and the other of which originates from a modifying group. Both the ester groups of the aforementioned aspirin prodrug can be rapidly cleaved by an enzyme in human plasma. Therefore, the above-mentioned aspirin prodrug may provide two enzymatically cleavaged products in plasma, namely the corresponding salicylic acid prodrug and acetylsalicylic acid. The above-mentioned patent alleges that, after entering the blood, the prodrug can be converted back into its parent drug, i.e. acetylsalicylic acid, instead of a salicylic acid derivative (i.e., a compound with the acetyl group removed). However, this is not the case in practice. As such, this compound is subject to great limitations in use.

Therefore, there is an urgent need in the art to find a new acetylsalicylic acid prodrug which can overcome the limitations of existing compounds.

SUMMARY

In order to solve the above technical problem, one aspect of the present disclosure provides a compound represented by Formula 1,

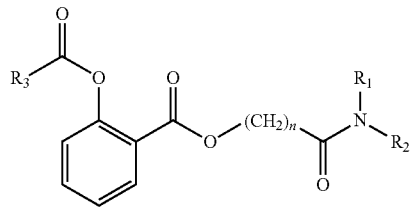

wherein $R_1$ and $R_2$ each independently represent H, substituted or unsubstituted $C_1$-$C_{30}$ alkyl, substituted or unsubstituted $C_1$-$C_{30}$ alkoxy, substituted or unsubstituted $C_2$-$C_{30}$ alkenyl, substituted or unsubstituted $C_6$-$C_{30}$ aryl, substituted or unsubstituted $C_7$-$C_{30}$ aralkyl, or substituted or unsubstituted $C_3$-$C_{30}$ cycloalkyl, or $R_1$ and $R_2$ form 4-, 5-, 6- or 7-membered heterocycle, together with the N to which they are linked;

$R_3$ represents substituted or unsubstituted $C_1$-$C_{12}$ alkyl;

n represents an integer of 0-20.

In a preferred embodiment of the present application, $R_1$ and $R_2$ each independently represent substituted or unsubstituted $C_1$-$C_{30}$ alkyl, preferably substituted or unsubstituted $C_1$-$C_{20}$ alkyl, more preferably substituted or unsubstituted $C_1$-$C_{15}$ alkyl, still more preferably substituted or unsubstituted $C_1$-$C_{10}$ alkyl, most preferably substituted or unsubstituted $C_1$-$C_6$ alkyl (such as methyl or ethyl); or $R_1$ and $R_2$ each independently represent substituted or unsubstituted $C_1$-$C_{30}$ alkoxy, preferably substituted or unsubstituted $C_1$-$C_{20}$ alkoxy, more preferably substituted or unsubstituted $C_1$-$C_{15}$ alkoxy, still more preferably substituted or unsubstituted $C_1$-$C_{10}$ alkoxy, most preferably substituted or unsubstituted $C_1$-$C_6$ alkoxy; or $R_1$ and $R_2$ each independently represent substituted or unsubstituted $C_2$-$C_{30}$ alkenyl, preferably substituted or unsubstituted $C_2$-$C_{20}$ alkenyl, more preferably substituted or unsubstituted $C_2$-$C_{15}$ alkenyl, still more preferably substituted or unsubstituted $C_2$-$C_{10}$ alkenyl, and most preferably substituted or unsubstituted $C_2$-$C_6$ alkenyl; or $R_1$ and $R_2$ each independently represent substituted or unsubstituted $C_6$-$C_{30}$ aryl, preferably substituted or unsubstituted $C_6$-$C_{20}$ aryl, more preferably substituted or unsubstituted $C_6$-$C_{15}$ aryl, most preferably substituted or unsubstituted $C_6$-$C_{10}$ aryl; or $R_1$ and $R_2$ each independently represent substituted or unsubstituted $C_7$-$C_{30}$ aralkyl, preferably substituted or unsubstituted $C_7$-$C_{20}$ aralkyl, more preferably substituted or unsubstituted $C_7$-$C_{15}$ aralkyl group, and most preferably substituted or unsubstituted $C_7$-$C_{10}$ aralkyl; or $R_1$ and $R_2$ each independently represent substituted or unsubstituted $C_3$-$C_{30}$ cycloalkyl, preferably substituted or unsubstituted $C_3$-$C_{20}$ cycloalkyl, more preferably substituted or unsubstituted $C_3$-$C_{10}$ cycloalkyl, most preferably substituted or unsubstituted $C_3$-$C_6$ cycloalkyl.

In a preferred embodiment of the present application, $R_3$ represents substituted or unsubstituted $C_1$-$C_{12}$ alkyl, preferably substituted or unsubstituted $C_1$-$C_6$ alkyl, more preferably substituted or unsubstituted $C_1$-$C_4$ alkyl, most preferably methyl.

In a preferred embodiment of the present application, n is preferably an integer of 1-20, more preferably an integer of 2-15, still preferably 2-10, most preferably 1, 2, 3, 4, 5, or 6.

In a preferred embodiment of the present application, the substituents in the substituted groups include deuterium, halogen, cyano, carboxyl, nitro, hydroxyl, ($C_1$-$C_{30}$) alkyl (preferably ($C_1$-$C_6$) alkyl), ($C_2$-$C_{30}$) alkenyl (preferably ($C_2$-$C_6$) alkenyl), ($C_1$-$C_{30}$) alkoxy (preferably ($C_1$-$C_6$) alkoxy), ($C_1$-$C_{30}$) alkylthio (preferably ($C_1$-$C_6$) alkylthio), ($C_3$-$C_{30}$) cycloalkyl (preferably ($C_3$-$C_6$) cycloalkyl), ($C_6$-$C_{30}$) aryl (preferably ($C_6$-$C_{14}$) aryl or $C_6$ aryl or phenyl) or amino.

In a preferred embodiment of the present application, the compound represented by Formula (1) is selected from:
2-[2-(acetoxy)benzoyloxy]-N,N-diethylacetamide,
2-[2-(acetoxy)benzoyloxy]-N,N-dimethylacetamide,
2-[2-(acetoxy)benzoyloxy]-N-ethylacetamide,
2-[2-(acetoxy)benzoyloxy]-N-methylacetamide,
2-[2-(acetoxy)benzoyloxy]-acetylcycloethylamine,
2-[2-(acetoxy)benzoyloxy]-acetylpiperidine,
3-[2-(acetoxy)benzoyloxy]-N,N-diethylpropionamide,
3-[2-(acetoxy)benzoyloxy]-N,N-dimethylpropionamide,
4-[2-(acetoxy)benzoyloxy]-N,N-diethylbutanamide,
4-[2-(acetoxy)benzoyloxy]-N,N-dimethylbutanamide,
5-[2-(acetoxy)benzoyloxy]-N,N-diethylvaleramide,
5-[2-(acetoxy)benzoyloxy]-N,N-dimethylvaleramide.

In another aspect of the present disclosure, there is provided a crystal of a compound represented by Formula (1) of the present application or a pharmaceutically acceptable salt thereof (e.g. 2-[2-(acetoxy)benzoyloxy]-N,N-diethylacetamide), wherein the crystal has characteristic peaks in an X-ray powder diffraction (XRPD) pattern at the following 2θ angles: 12.2°±0.2°, 18.1°±0.2°, 21.8°±0.2°, 24.4°±0.2°, 29.4°±0.2°, 30.6°±0.2°, 31.9° 0.2°, 36.6°±0.2°. Alternatively, the crystal has characteristic peaks in an X-ray powder diffraction (XRPD) pattern at the following 2θ angles: 9.4°±0.2°, 10.3°±0.2°, 12.2°±0.2°, 18.1°±0.2°, 21.8°±0.2°, 24.4°±0.2°, 29.4°±0.2°, 30.6°±0.2°, 31.9°±0.2°, 36.6°±0.2°.

Preferably, the crystal further has characteristic peaks in an X-ray powder diffraction (XRPD) pattern at the following 2θ angles: 20.4°±0.2°, 25.8°±0.2°, 27.0°±0.2°, 28.4°±0.2°, 28.8°±0.2°, 32.9°±0.2°.

In an embodiment of the present disclosure, there is provided a crystal of 2-[2-(acetoxy)benzoyloxy]-N,N-diethylacetamide with X-ray powder diffraction results thereof shown in Table 5 below.

In an embodiment, the conditions under which the X-ray powder diffraction of the present disclosure is measured include: Cu-Kα, test temperature: 25° C. More preferably, the conditions under which the X-ray powder diffraction of the present disclosure is measured further include: tube pressure/tube current: 40 kV-45 kV/40 mA; scanning angle: 3°-60°. Still more preferably, the instrument used for the X-ray powder diffraction is: Panalytical X' Pert Powder powder X-ray diffractometer.

In still another aspect of the present disclosure, there is provided a pharmaceutical composition, comprising a therapeutically effective amount of a compound represented by Formula (1) or a pharmaceutically acceptable salt thereof, or a crystal of a compound represented by Formula (1) of the present application or a pharmaceutically acceptable salt thereof, and a pharmaceutically acceptable carrier. In a preferred embodiment, the pharmaceutical composition consists of a therapeutically effective amount of a compound represented by Formula (1) or a pharmaceutically acceptable salt thereof, or a crystal of a compound represented by Formula (1) of the present application or a pharmaceutically acceptable salt thereof, and a pharmaceutically acceptable carrier. Preferably, a dosage form of the pharmaceutical composition is a transdermal dosage form or a transmucosal dosage form. Alternatively, a dosage form of the pharmaceutical composition is selected from the group consisting of patch, suppository, drop, liniment, gel, ointment, spray, aerosol, or powder.

In a preferred embodiment of the present application, the pharmaceutical composition is used to treat acetylsalicylic acid indications. Preferably, the indications of acetylsalicylic acid include pain, fever, inflammation, rheumatism, arthritis, cancer, diabetes or its complications, dementia, cardiovascular diseases, cerebrovascular diseases. Alternatively, the pharmaceutical composition is used for anti-platelet aggregation. Alternatively, the pharmaceutical composition is used for prevention of cardiovascular and cerebrovascular diseases.

In another aspect of the present disclosure, there is provided use of a compound represented by Formula (1) or a pharmaceutically acceptable salt thereof, or a crystal of a compound represented by Formula (1) of the present application or a pharmaceutically acceptable salt thereof in preparation of a drug for treatment of acetylsalicylic acid indications. Preferably, a dosage form of the drug is a transdermal dosage form or a transmucosal dosage form. Alternatively, a dosage form of the drug is selected from the group consisting of patch, suppository, drop, liniment, gel, ointment, spray, aerosol, or powder.

In a preferred embodiment of the present application, the acetylsalicylic acid indications include pain, fever, inflammation, rheumatism, arthritis, cancer, diabetes or its complications, dementia, cardiovascular diseases, cerebrovascular diseases. Alternatively, the drug is an anti-platelet aggregation drug. Alternatively, the drug is used to prevent cardiovascular and cerebrovascular diseases. Alternatively, a subject of the use is a primate (such as a monkey or a human being), preferably a human being.

DETAILED DESCRIPTION

Figure 1:
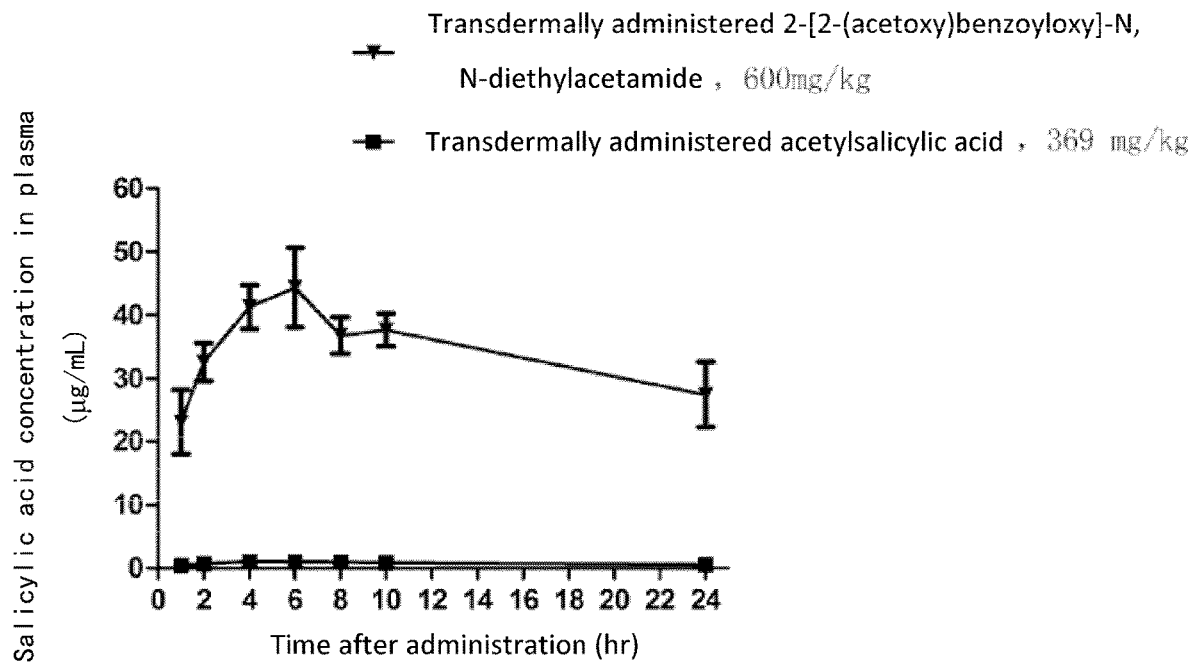
FIG. 1 depicts the plasma concentrations of 2-[2-(acetoxy)benzoyloxy]-N,N-diethylacetamide and acetylsalicylic acid in rats after transdermal administration.

In this specification, unless otherwise specified particularly, the components or their preferred components involved may be combined with each other to form new technical solutions.

In this specification, unless otherwise specified particularly, all the embodiments and the preferred embodiments mentioned herein may be combined with each other to form new technical solutions.

In this specification, unless otherwise specified particularly, all the technical features and the preferred features mentioned herein may be combined with each other to form new technical solutions.

In this specification, unless otherwise specified to the contrary, a sum of the contents of the components in a composition is 100%.

In this specification, unless otherwise specified to the contrary, a sum of the parts of the components in a composition may be 100 parts by weight.

In this specification, unless otherwise specified, the numerical range "a-b" is an abbreviated representation of any combination of real numbers between a and b, wherein both a and b are real numbers. For example, the numerical range "0-5" means that all real numbers between "0-5" have been listed herein, and "0-5" is only an abbreviated representation of these numerical combinations.

In this specification, unless otherwise specified, the integer value range "a-b" is an abbreviated representation of any combination of integers between a and b, wherein both a and b are integers. For example, the integer value range "1-N" represents 1, 2 ... N, wherein N is an integer.

In this specification, unless otherwise specified, "combination thereof" means a multi-component mixture of the respective elements, such as mixtures of two, three, four, and up to the largest possible number of components.

Unless otherwise specified, the term "a" used in this specification means "at least one".

Unless otherwise specified, the percentages (including weight percentages) in this specification are based on the total weight of the composition.

In this specification, unless otherwise specified, the term "$C_n$-$C_m$" represents an organic group, wherein n and m are integers, and each group may contain n to m carbon atoms.

In this specification, unless otherwise specified, the term "alkyl" means a saturated hydrocarbon group which may be linear or branched, such as methyl, ethyl, n-propyl, isopropyl, n-butyl, sec-butyl, tert-butyl, amyl and n-hexyl.

In this specification, unless otherwise specified, the term "cycloalkyl" means a saturated hydrocarbon group containing one or more cycloalkyl rings, such as cyclopentyl, cyclooctyl, and adamantyl.

In this specification, unless otherwise specified, the term "alkoxy" means a monovalent group —RO (for example, a methoxy group) composed of an alkyl group plus an oxygen atom.

In this specification, unless otherwise specified, the term "aryl" means a monovalent unsaturated hydrocarbon group containing one or more six-membered carbon rings, wherein the degree of unsaturation may be represented by three conjugate acid-base pairs, wherein one or more carbon atoms in the ring(s) of the aryl group may be substituted with hydroxyl, alkyl, alkenyl, halogen, haloalkyl, monocyclic aryl or amino, such as but not limited to phenyl, methylphenyl, methoxy phenyl, dimethylphenyl, trimethylphenyl, chlorophenyl, trichloromethylphenyl, triisobutylphenyl, tristyrylphenyl, and aminophenyl.

In this specification, unless otherwise specified, the term "aralkyl" means an alkyl group substituted with one or more aryl groups, for example, ($C_1$-$C_{18}$) alkyl substituted with one or more ($C_6$-$C_{14}$) aryl groups, such as phenylmethyl, phenylethyl and triphenylmethyl.

In this specification, unless otherwise specified, the term "alkenyl" means an unsaturated linear or branched hydrocarbon group containing one or more carbon-carbon double bonds, for example, an unsaturated linear or branched ($C_2$-$C_{22}$) hydrocarbon group, such as vinyl, n-propenyl and isopropenyl.

In this specification, unless otherwise specified, the term "substitute" or "substituted" or the like means that the group contains one or more substituents which include but are not limited to deuterium, halogen, cyano, carboxyl, nitro, hydroxyl, ($C_1$-$C_{30}$) alkyl (preferably ($C_1$-$C_6$) alkyl), ($C_2$-$C_{30}$) alkenyl (preferably ($C_2$-$C_6$) alkenyl), ($C_1$-$C_{30}$) alkoxy (preferably ($C_1$-$C_6$) alkoxy), ($C_1$-$C_{30}$) alkylthio (preferably ($C_1$-$C_6$) alkylthio), ($C_3$-$C_{30}$) cycloalkyl (preferably ($C_3$-$C_6$) cycloalkyl), ($C_6$-$C_{30}$) aryl (preferably ($C_6$-$C_{14}$) aryl or $C_6$ aryl or phenyl) or amino.

The "range" disclosed herein is formed with a lower limit and/or an upper limit. There may be one or more lower limits, and one or more upper limits, respectively. A given range is defined by selecting a lower limit and an upper limit. The selected lower and upper limits define the boundary of the particular range. All ranges that can be defined this way are inclusive and combinable, that is, any lower limit can be combined with any upper limit to form a range. For example, if the ranges of 60-120 and 80-110 are listed for a particular parameter, it should be appreciated that the ranges of 60-110 and 80-120 are also contemplated. In addition, if 1 and 2 are listed as the possible minimum values of a range, and if 3, 4, and 5 are listed as the possible maximum values of that range, the following ranges can all be contemplated: 1-3, 1-4, 1-5, 2-3, 2-4, and 2-5.

In particular, the present disclosure provides a compound represented by Formula (1) or a pharmaceutically acceptable salt thereof,

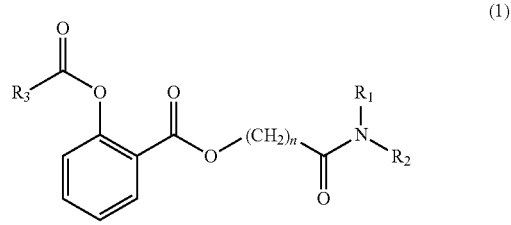

wherein $R_1$ and $R_2$ each independently represent H, substituted or unsubstituted $C_1$-$C_{30}$ alkyl, substituted or unsubstituted $C_1$-$C_{30}$ alkoxy, substituted or unsubstituted $C_2$-$C_{30}$ alkenyl, substituted or unsubstituted $C_6$-$C_{30}$ aryl, substituted or unsubstituted $C_7$-$C_{30}$ aralkyl, or substituted or unsubstituted $C_3$-$C_{30}$ cycloalkyl, or $R_1$ and $R_2$ form 4-, 5-, 6- or 7-membered heterocycle, together with the N to which they are linked;

$R_3$ represents substituted or unsubstituted $C_1$-$C_{12}$ alkyl;

n represents an integer of 0-20.

In an embodiment of this specification, $R_1$ and $R_2$ each independently represent substituted or unsubstituted $C_1$-$C_{30}$ alkyl, preferably substituted or unsubstituted $C_1$-$C_{20}$ alkyl, more preferably substituted or unsubstituted $C_1$-$C_{15}$ alkyl, still more preferably substituted or unsubstituted $C_1$-$C_{10}$ alkyl, and most preferably substituted or unsubstituted $C_1$-$C_6$ alkyl. In another embodiment of this specification, $R_1$ and $R_2$ each independently represent methyl, ethyl, n-propyl, isopropyl, n-butyl, isobutyl, or tert-butyl.

In an embodiment of this specification, $R_1$ and $R_2$ each independently represent substituted or unsubstituted $C_1$-$C_{30}$ alkoxy, preferably substituted or unsubstituted $C_1$-$C_{20}$ alkoxy, more preferably substituted or unsubstituted $C_1$-$C_{15}$ alkoxy, still more preferably substituted or unsubstituted $C_1$-$C_{10}$ alkoxy, and most preferably substituted or unsubstituted $C_1$-$C_6$ alkoxy. In another embodiment of this specification, $R_1$ and $R_2$ each independently represent methoxy, ethoxy, n-propoxy, isopropoxy, n-butoxy, isobutoxy or tert-butoxy.

In an embodiment of this specification, $R_1$ and $R_2$ each independently represent substituted or unsubstituted $C_2$-$C_{30}$ alkenyl, preferably substituted or unsubstituted $C_2$-$C_{20}$ alkenyl, more preferably substituted or unsubstituted $C_2$-$C_{15}$ alkenyl, still more preferably substituted or unsubstituted $C_2$-$C_{10}$ alkenyl, and most preferably substituted or unsubstituted $C_2$-$C_6$ alkenyl. In another embodiment of this specification, $R_1$ and $R_2$ each independently represent vinyl, propenyl, or butenyl.

In an embodiment of this specification, $R_1$ and $R_2$ each independently represent substituted or unsubstituted $C_6$-$C_{30}$ aryl, preferably substituted or unsubstituted $C_6$-$C_{20}$ aryl, more preferably substituted or unsubstituted $C_6$-$C_{15}$ aryl, most preferably substituted or unsubstituted $C_6$-$C_{10}$ aryl. In another embodiment of this specification, $R_1$ and $R_2$ each independently represent phenyl or naphthyl.

In an embodiment of this specification, $R_1$ and $R_2$ each independently represent substituted or unsubstituted $C_7$-$C_{30}$ aralkyl, preferably substituted or unsubstituted $C_7$-$C_{20}$ aralkyl, more preferably substituted or unsubstituted $C_7$-$C_{15}$ aralkyl, most preferably substituted or unsubstituted $C_7$-$C_{10}$ aralkyl. In another embodiment of this specification, $R_1$ and $R_2$ each independently represent phenylmethyl, phenylethyl, or naphthylmethyl.

In an embodiment of this specification, $R_1$ and $R_2$ each independently represent substituted or unsubstituted $C_3$-$C_{30}$ cycloalkyl, preferably substituted or unsubstituted $C_3$-$C_{20}$ cycloalkyl, more preferably substituted or unsubstituted $C_3$-$C_{10}$ cycloalkyl, most preferably substituted or unsubstituted $C_3$-$C_6$ cycloalkyl. In another embodiment of this specification, $R_1$ and $R_2$ each independently represent cyclopropyl, cyclobutyl, cyclopentyl or cyclohexyl.

In an embodiment of this specification, $R_3$ represents substituted or unsubstituted $C_1$-$C_{12}$ alkyl, preferably substituted or unsubstituted $C_1$-$C_6$ alkyl, more preferably substituted or unsubstituted $C_1$-$C_4$ alkyl, most preferably methyl.

In an embodiment of this specification, n represents an integer of 0-20, preferably an integer of 1-20, more preferably an integer of 2-15, still more preferably an integer of 2-10, and most preferably an integer of 2-6. In another embodiment of this specification, n represents 1, 2, 3, 4, 5, or 6.

In an embodiment of this specification, the substituents in the substituted groups include but are not limited to deuterium, halogen, cyano, carboxyl, nitro, hydroxyl, ($C_1$-$C_{30}$) alkyl (preferably ($C_1$-$C_6$) alkyl), ($C_2$-$C_{30}$) alkenyl (preferably ($C_2$-$C_6$) alkenyl), ($C_1$-$C_{30}$) alkoxy (preferably ($C_1$-$C_6$) alkoxy), ($C_1$-$C_{30}$) alkylthio (preferably ($C_1$-$C_6$) alkylthio), ($C_3$-$C_{30}$) cycloalkyl (preferably ($C_3$-$C_6$) cycloalkyl), ($C_6$-$C_{30}$) aryl (preferably ($C_6$-$C_{14}$) aryl or $C_6$ aryl or phenyl) or amino. In another embodiment of this specification, the substituents in the substituted groups includes but are not limited to halogen, cyano, nitro, hydroxyl, amino, ($C_1$-$C_6$) alkoxy or preferably ($C_1$-$C_6$) alkyl.

In an embodiment of this specification, the compound represented by Formula (1) is selected from:

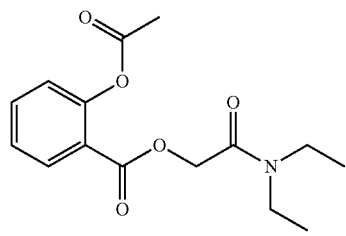

2-[2-(acetoxy)benzoyloxy]-N,N-diethylacetamide

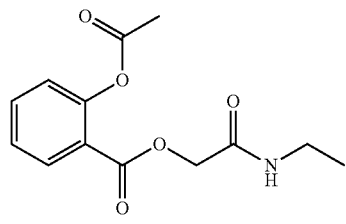

2-[2-(acetoxy)benzoyloxy]-N-ethylacetamide

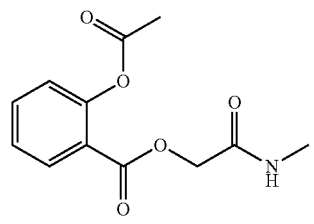

2-[2-(acetoxy)benzoyloxy]-N-methylacetamide

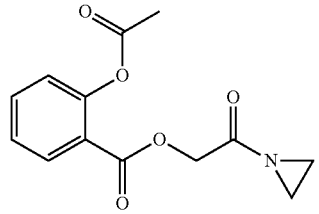

2-[2-(acetoxy)benzoyloxy]-acetylcycloethylamine

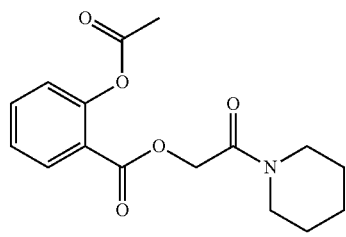

2-[2-(acetoxy)benzoyloxy]-acetylpiperidine

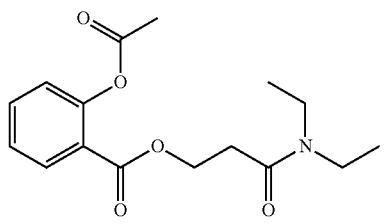

3-[2-(acetoxy)benzoyloxy]-N,N-diethylpropionamide

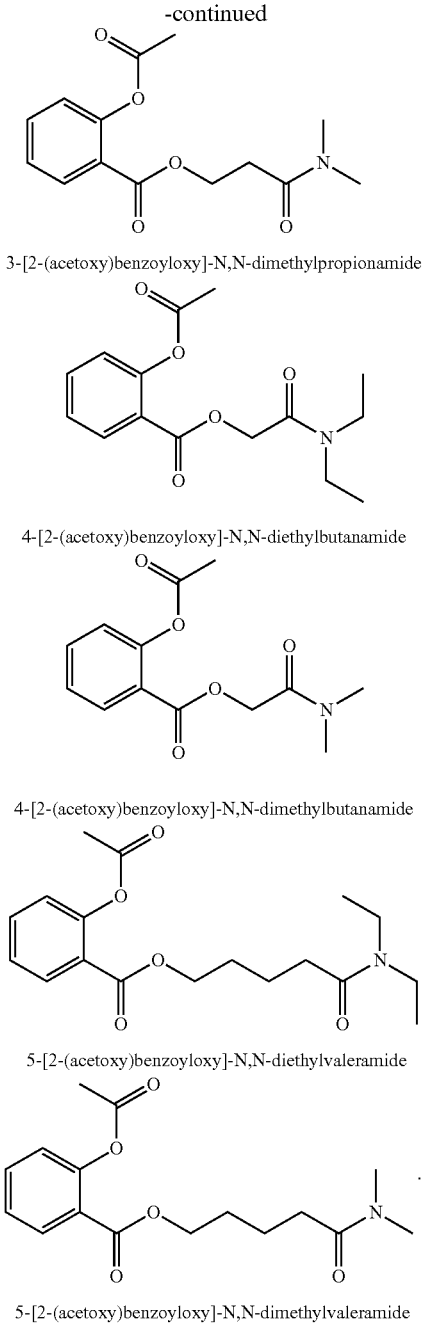

3-[2-(acetoxy)benzoyloxy]-N,N-dimethylpropionamide

4-[2-(acetoxy)benzoyloxy]-N,N-diethylbutanamide

4-[2-(acetoxy)benzoyloxy]-N,N-dimethylbutanamide

5-[2-(acetoxy)benzoyloxy]-N,N-diethylvaleramide

5-[2-(acetoxy)benzoyloxy]-N,N-dimethylvaleramide

In this specification, unless otherwise specified, the compound represented by Formula (1) generally includes its pharmaceutically acceptable salts, including but not limited to pharmaceutically acceptable hydrochloride, sulfate, acetate or nitrate.

Acetylsalicylic acid has been proved to have anti-inflammatory, analgesic, antipyretic, anti-rheumatic, and anti-platelet aggregation effects, while salicylic acid has only anti-inflammatory, analgesic and antipyretic effects.

As mentioned above, the aspirin derivative (i.e., aspirin prodrug) described in the present application comprises two ester bonds, one of which (an acetyl group) originates from salicylic acid itself, and the other of which originates from a modifying group. Both the ester groups of the aforementioned aspirin prodrug can be rapidly cleaved by an enzyme in human plasma. As confirmed by the following examples, the modifying group in the aspirin derivative described in the present application is first removed by the enzyme in the plasma, and then the acetyl group is removed. That is, acetylsalicylic acid (aspirin) is present in the plasma. As for the aspirin prodrug disclosed in CN 101484415B, the acetyl group is first removed in the plasma, and then the modifying group is removed. That is, acetylsalicylic acid (aspirin) does not exist in the plasma, or its amount is extremely low. Therefore, the aspirin derivative described in the present application can retain all the therapeutic effects of aspirin, whereas the aspirin prodrug disclosed in CN 101484415 B can only retain the therapeutic effects of salicylic acid.

The Chinese Patent CN 101484415B mentions that, after entering the blood, the aspirin prodrug can be converted back into its parent drug, i.e. acetylsalicylic acid, instead of a salicylic acid derivative (i.e., a compound with the acetyl group removed). However, according to the test method used in this patent, the whole blood is diluted by 20 times, which reduces the activity of the enzyme in the plasma. In the case of a low dilution fold (such as 10 times described in the present application; see the following examples for details) or in vivo experiments (i.e. not diluted; see the following examples for details), after the aspirin prodrug described in CN 101484415B enters blood, there is not a large amount of aspirin (acetylsalicylic acid), or the effect of anti-platelet aggregation does not show up.

The compound represented by Formula (1) of the present application or a pharmaceutically acceptable salt thereof, or a crystal of a compound represented by Formula (1) of the present application or a pharmaceutically acceptable salt thereof can enter blood via transdermal or transmucosal administration, and it is metabolized into acetylsalicylic acid in the plasma of a primate (e.g., a monkey, a human being). Therefore, the compound represented by Formula (1) in the present application or a pharmaceutically acceptable salt thereof really has the effects of its corresponding original drug (aspirin) as a non-steroidal anti-inflammatory drug (e.g., anti-inflammation, analgesia, antipyresis, anti-platelet aggregation). At the same time, it can avoid gastrointestinal adverse reactions caused by oral administration of a common non-steroidal anti-inflammatory drug.

The compound represented by Formula (1) of the present application or a pharmaceutically acceptable salt thereof, or a crystal of a compound represented by Formula (1) of the present application or a pharmaceutically acceptable salt thereof can treat acetylsalicylic acid (aspirin) indications, including pain, fever, inflammation, rheumatism, arthritis, cancer, diabetes or its complications, dementia, cardiovascular diseases, cerebrovascular diseases. In particular, the compound represented by Formula (1) or a pharmaceutically acceptable salt thereof, or a crystal of a compound represented by Formula (1) of the present application or a pharmaceutically acceptable salt thereof can be used as a drug to prevent platelet aggregation, because anti-platelet aggregation is exactly one of the pharmacodynamic effects of acetylsalicylic acid, not among those of salicylic acid. In addition, anti-platelet aggregation is also the key to the treatment or prevention of cardiovascular and cerebrovascular diseases.

In an embodiment of the present specification, the acetylsalicylic acid indication is selected from pain, fever, inflammation, rheumatism, arthritis, cancer, diabetes or its complications, dementia, cardiovascular diseases, and cerebrovascular diseases. In another embodiment, the treatment of the acetylsalicylic acid indication is to prevent platelet aggregation.

In another aspect of the present disclosure, there is further provided a pharmaceutical composition, comprising a therapeutically effective amount of a compound represented by Formula (1) or a pharmaceutically acceptable salt thereof, or a crystal of a compound represented by Formula (1) of the present application or a pharmaceutically acceptable salt thereof, and a pharmaceutically acceptable carrier. Preferably, the pharmaceutical composition consists of a therapeutically effective amount of a compound represented by Formula (1) or a pharmaceutically acceptable salt thereof, or a crystal of a compound represented by Formula (1) of the present application or a pharmaceutically acceptable salt thereof, and a pharmaceutically acceptable carrier.

In this specification, unless otherwise specified, the term "comprising . . . " means that the pharmaceutical composition may further contain any other components, and these components may be present in any amount, as long as the component present in that amount is acceptable to the human body and has no negative influence on the activity of the active ingredient in the pharmaceutical composition of the present disclosure.

In this specification, unless otherwise specified, the term "pharmaceutically acceptable carrier" shall be compatible with the active ingredient (the compound represented by Formula (1) or a pharmaceutically acceptable salt thereof) in the pharmaceutical composition of the present disclosure. That is, it can be blended with active ingredient without significantly reducing the therapeutic effect of the drug under normal circumstances. The "pharmaceutically acceptable carriers" include but are not limited to: sugars, such as lactose, glucose, sucrose, trehalose; starch, such as corn starch, potato starch; cellulose or its derivatives, such as sodium carboxymethyl cellulose, ethyl cellulose, methyl cellulose; tragacanth powder; gelatin; talc powders; vaseline; solid lubricants, such as stearic acid, magnesium stearate; calcium sulfate; vegetable oils, such as peanut oil, cottonseed oil, sesame oil, olive oil, corn oil, cocoa oil; alcohols, such as ethanol, propylene glycol, glycerin, sorbitol, mannitol, polyethylene glycol; aminocaproic acid, alginic acid; emulsifiers, such as Tween; wetting agents, such as sodium lauryl sulfate; coloring agents; flavoring agents; tableting aids; antioxidants; medicinal preservatives; pyrogen-free water; isotonic salt solutions; buffers; etc.; or combinations thereof.

In an embodiment, the pharmaceutical composition is used to treat acetylsalicylic acid indications. In another embodiment, the pharmaceutical composition is used to treat pain, fever, inflammation, rheumatism, arthritis, cancer, diabetes or its complications, dementia, cardiovascular diseases, and cerebrovascular diseases. In still another embodiment, the pharmaceutical composition is used to prevent platelet aggregation. Alternatively, the pharmaceutical composition is used to prevent cardiovascular and cerebrovascular diseases.

Preferably, the pharmaceutical composition is administered via transdermal administration or transmucosal administration. The subject to which the pharmaceutical composition is administered is a primate, more preferably a human being. The dosage form of the pharmaceutical composition is a transdermal dosage form or a transmucosal dosage form. More preferably, the dosage form of the pharmaceutical composition is selected from the group consisting of patch, suppository, drop, liniment, gel, ointment, spray, aerosol, or powder.

In a specific embodiment, the pharmaceutical composition is a 5% liniment comprising a compound represented by Formula (1) or a pharmaceutically acceptable salt thereof, or a crystal of a compound represented by Formula (1) of the present application or a pharmaceutically acceptable salt thereof dissolved in 50% ethanol. When the liniment is used, a patient may apply it to the skin of the trunk or limbs, twice a day, 0.5-2 mL each time, to prevent the occurrence of cardiovascular or cerebrovascular diseases (anti-platelet aggregation effect). In yet another aspect of the present application, there is provided use of a compound represented by Formula (1) or its pharmaceutically acceptable salt or a crystal of a compound represented by Formula (1) of the present application or its pharmaceutically acceptable salt in preparation of a drug for treatment of acetylsalicylic acid indications; or there is provided use of a compound represented by Formula (1) or its pharmaceutically acceptable salt or a crystal of a compound represented by Formula (1) of the present application or its pharmaceutically acceptable salt in treatment of acetylsalicylic acid indications; or there is provided a compound represented by Formula (1) or a pharmaceutically acceptable salt thereof or a crystal of a compound represented by Formula (1) of the present application or a pharmaceutically acceptable salt thereof for treatment of acetylsalicylic acid indications; or there is provided a method of using a compound represented by Formula (1) or a pharmaceutically acceptable salt thereof or a crystal of a compound represented by Formula (1) of the present application or a pharmaceutically acceptable salt thereof to treat acetylsalicylic acid indications.

In an embodiment, the acetylsalicylic acid (aspirin) indication is selected from pain, fever, inflammation, rheumatism, arthritis, cancer, diabetes or its complications, dementia, cardiovascular diseases, and cerebrovascular diseases. In particular, the compound represented by Formula (1) or a pharmaceutically acceptable salt thereof, or a crystal of a compound represented by Formula (1) of the present application or a pharmaceutically acceptable salt thereof can be used as a drug to prevent platelet aggregation, because anti-platelet aggregation is exactly the pharmacodynamic effect of acetylsalicylic acid, not the pharmacodynamic effect of salicylic acid.

In an embodiment, the acetylsalicylic acid indication is selected from pain, fever, inflammation, rheumatism, arthritis, cancer, diabetes or its complications, dementia, cardiovascular diseases, and cerebrovascular diseases. In another embodiment, the treatment of the acetylsalicylic acid indication is to prevent platelet aggregation. In yet another embodiment, the drug is used to prevent cardiovascular and cerebrovascular diseases.

In an embodiment of the present application, the subject of the use or method is a primate (such as a monkey or a human being), preferably a human being.

The present application further provides a crystal form of the compound represented by Formula (1) or a pharmaceutically acceptable salt thereof. Preferably, there is provided a crystal form of 2-[2-(acetoxy)benzoyloxy]-N,N-diethylacetamide. See Example 1 for the specific preparation method of this crystal form. In a preferred embodiment of the present application, the crystal form is obtained by recrystallizing the compound represented by Formula (1) or a pharmaceutically acceptable salt thereof in an organic solvent (preferably ethyl acetate/petroleum ether).

The present disclosure will be further described in detail with reference to the following examples. However, it should be understood that these examples are listed only for the purpose of illustration, not for limiting the scope of the present disclosure.

Example 1: Preparation of 2-[2-(acetoxy)benzoyloxy]-N,N-diethylacetamide

Acetylsalicylic acid (360.23 g, 2.0 mol, 1.0 eq) and 2-chloro-diethylacetamide (299.89 g, 2.0 mol, 1.0 eq) were added into a 3 L three-necked flask, and dissolved in ethyl acetate (1.5 L). Triethylamine (202.34 g, 2.0 mol, 1.0 eq) and sodium iodide (30.21 g, 0.2 mol, 0.1 eq) were added, stirred and warmed up. When the oil bath temperature was raised to 80° C., refluxing was started. The stirring was continued for 4 hours. The resultant solution was cooled to room temperature, and filtered. The filtrate was washed with 2 M HCl (800 mL), a 5% aqueous solution of sodium bicarbonate (800 mL) and a saturated solution of sodium chloride (800 mL), and dried with anhydrous sodium sulfate for 4 hours. Filtration was performed, and the filtrate was concentrated to obtain a yellow solid. That is, a crude product of the target compound was obtained.

Under the heating and refluxing conditions, a mixed liquid of ethyl acetate/petroleum ether (1/1, V/V) was continuously added to the crude product of the target compound, and stirred and mixed until the crude product was completely dissolved. The final mass-volume ratio of the crude product of the target compound to the mixed liquid of ethyl acetate/petroleum ether (1/1, V/V) was 1:3. After slow cooling to 25° C., white crystals were precipitated out, and the solid was subjected to vacuum spin-drying after suction filtration.

HPLC: 99.8% (271 nm), yield: 37.2%; melting point: 76.0-77.0° C.

HNMR (CDCl3): δ(ppm): 8.15 (dd, J=8.0, 2.0 Hz, 1H), 7.58-7.54 (m, 1H), 7.31 (td, J=7.5, 1.0 Hz, 1H), 7.11 (dd, J=6.0, 2.0 Hz, 1H), 4.80 (s, 2H), 3.41 (q, J=7.0 Hz, 2H), 3.29 (q, J=7.0 Hz, 2H), 2.34 (s, 3H), 1.24 (t, J=7.0 Hz, 3H), 1.15 (t, J=7.0 Hz, 3H).

CNMR (CDCl3): δ(ppm): 169.7, 165.2, 164.0, 150.8, 134.0, 132.1, 126.0, 123.7, 122.8, 61.8, 41.0, 40.4, 19.0, 14.2, 12.9.

Example 2: Transdermal Test of 2-[2-(acetoxy)benzoyloxy]-N,N-diethylacetamide in Rats 12 SD rats were divided into 2 groups, namely an acetylsalicylic acid transdermal administration group and a 2-[2-(acetoxy)benzoyloxy]-N,N-diethylacetamide transdermal administration group. Grouping and dosing information were shown in Table 1:

TABLE 1

| Group | Dosage (mg/kg) | Number | Dosing volume (mL) |
|---|---|---|---|
| 10% 2-[2-(acetoxy)benzoyloxy]-N,N-diethylacetamide in NMP | 600 | 6 | 1.2 |
| 6.15% acetylsalicylic acid in NMP | 369 | 6 | 1.2 |

Note 1:
The weight of a rat was taken as 200 g.
Note 2:
NMP: N-methylpyrrolidone.
Note 3:
The two compounds were applied in equimolar dosages.

The test steps were as follows:

1) Depilation and grouping: After the rats were adaptively fed, the backs of the rats were depilated with a pet depilator. After weighing, they were randomly divided into 2 groups according to body weight.

2) Administration: A pipette was used to draw 1.2 mL of the two compound solutions, which were evenly on the depilated areas, respectively. After the administration, the rats each were raised in a single cage.

3) Blood collection: at the time of 1, 2, 4, 6, 8, 10, and 24 hours after administration, respectively, 0.3 ml blood was collected into an anticoagulation EP tube, and centrifuged at 8000 rpm for 5 minutes to separate the plasma.

4) HPLC analysis: 50 μl plasma was transferred into a centrifuge tube containing 300 μl acetonitrile, vortex mixed uniformly, and centrifuged at 12000 rpm for 10 minutes at 4° C. The supernatant was passed through a 0.22 m organic phase filter membrane for HPLC assay to determine the concentration of salicylic acid in the plasma (the half-life of acetylsalicylic acid in plasma in vivo was so short that it was difficult to determine the concentration of acetylsalicylic acid, so an alternative was to determine the concentration of salicylic acid in plasma).

5) HPLC mobile phase conditions: 0.1% trifluoroacetic acid aqueous phase (1000 ml water+1 ml trifluoroacetic acid):acetonitrile=55:54 isocratic elution.

The experimental results were shown in FIG. 1. As shown by the results, after transdermal administration of 2-[2-(acetoxy)benzoyloxy]-N,N-diethylacetamide to SD rats, the $C_{max}$ of salicylic acid in the plasma was 44.37 μg/mL; whereas the $C_{max}$ of salicylic acid in the plasma was 1.06 μg/mL after transdermal administration of equimolar dosages of acetylsalicylic acid. Therefore, the transdermal performance of 2-[2-(acetoxy)benzoyloxy]-N,N-diethylacetamide in rats is much better than that of acetylsalicylic acid.

Example 3: Plasma Metabolic Stability Test of 2-[2-(acetoxy)benzoyloxy]-N,N-diethylacetamide and 2-(diethylamino)-ethyl-2-acetoxybenzoate Hydrochloride A desirable acetylsalicylic acid derivative should be able to be quickly converted back to acetylsalicylic acid in plasma. We compared 2-[2-(acetoxy)benzoyloxy]-N,N-diethylacetamide with another acetylsalicylic acid derivative 2-(diethylamino)ethyl-2-acetoxybenzoate hydrochloride disclosed in Chinese Patent CN 101484415B to determine the conversion rates of these two acetylsalicylic acid derivatives.

29.30 mg 2-[2-(acetoxy)benzoyloxy]-N,N-diethylacetamide powder was weighed and dissolved in a 1 mL acetonitrile solution to formulate a stock solution with a concentration of 100 μM/mL for further use. 31.58 mg 2-(diethylamino)-ethyl-2-acetoxybenzoate hydrochloride powder was weighed and dissolved in 1 mL ddH₂O to formulate a stock solution with a concentration of 100 μM/mL for further use. 50 μl of each of the 2-[2-(acetoxy)benzoyloxy]-N,N-diethylacetamide stock solution and the 2-(diethylamino)-ethyl-2-acetoxybenzoate hydrochloride stock solution (both at a concentration of 100 μM/mL) was transferred into 5 mL of a 10% monkey plasma diluent respectively. Both of the diluted drugs had a concentration of 1 μM/mL, and they were subjected to incubation reaction at 37° C. HPLC assay was performed at the time of 0 min, 5 min, 15 min, 30 min, 60 min, 120 min, 240 min after the plasma diluent was mixed with 2-[2-(acetoxy)benzoyloxy]-N,N-diethylacetamide uniformly. HPLC assay was performed at the time of 0 min, 10 min, 30 min, 60 min, 120 min, 240 min, 360 min, and 480 min after the plasma diluent was mixed with 2-(diethylamino)-ethyl-2-acetoxybenzoate hydrochloride uniformly. HPLC mobile phase conditions:

0.1% trifluoroacetic acid aqueous phase (1000 mL water+1 mL trifluoroacetic acid):acetonitrile=55:54 isocratic elution.

Upon calculation, the results showed that the initial concentration of the parent drug 2-[2-(acetoxy)benzoyloxy]-N,N-diethylacetamide was 221.81 μg/mL, and the concentration decreased to 179.97 μg/mL within 5 min. After 15 min, it was undetectable. The highest concentration of the metabolite, namely acetylsalicylic acid, was 141.83 μg/ml (equivalent to 0.7872 μM/mL), which appeared at the time of 30 min, and the conversion rate was 78.72%. See Table 2 for details.

Conversion rate of acetylsalicylic acid=(molar concentration of acetylsalicylic acid/initial molar concentration of drug)×100%

Note: The initial molar concentration of the drug here was 1 μM/mL.

TABLE 2

| Time | Acetylsalicylic acid (μg/ml) | Salicylic acid (μg/ml) |
|---|---|---|
| 0 min | 5.32 | 0.27 |
| 5 min | 56.74 | 11.45 |
| 15 min | 139.88 | 42.15 |
| 30 min | 141.83 | 44.60 |
| 60 min | 135.97 | 47.59 |
| 120 min | 112.72 | 51.64 |
| 240 min | 104.85 | 61.89 |

Upon calculation, the results showed that the initial concentration of the parent drug 2-(diethylamino)-ethyl-2-acetoxybenzoate hydrochloride was 261.90 μg/mL, and the concentration decreased to 3.09 μg/mL after 10 min. It was undetectable at the time of 30 min. The highest concentration of the metabolite, namely acetylsalicylic acid, was 8.09 μg/mL (equivalent to 0.0449 μM/mL), which appeared at the time of 10 min, and the highest conversion rate was 4.49%. See Table 3 for details.

TABLE 3

| Time | Acetylsalicylic acid (μg/ml) | Salicylic acid (μg/ml) |
|---|---|---|
| 0 min | 1.75 | 1.08 |
| 10 min | 8.09 | 106.91 |
| 30 min | 7.86 | 161.00 |
| 60 min | 7.74 | 161.99 |
| 120 min | 7.15 | 163.24 |
| 240 min | 5.78 | 164.55 |
| 360 min | 5.56 | 166.57 |
| 480 min | 4.44 | 161.63 |

In addition to the investigation on the metabolism of 2-[2-(acetoxy)benzoyloxy]-N,N-diethylacetamide and 2-(diethylamino)-ethyl-2-acetoxybenzoate hydrochloride in monkey plasma, the inventors also tested the metabolism of these two compounds in 10% diluted plasma of other species. The detailed results were shown in Table 4. As shown by the results, in comparison with rodents (rats, mice), dogs, etc., the conversion rate of 2-[2-(acetoxy)benzoyloxy]-N,N-diethylacetamide into acetylsalicylic acid in the plasma of primates (including human beings) is very high, indicating that the metabolism is species-specific. In contrast, the conversion rate of 2-(diethylamino)-ethyl-2-acetoxybenzoate hydrochloride into acetylsalicylic acid in the plasma of all species tested is less than 6%, and it is mainly metabolized into salicylic acid in every case.

TABLE 4

Comparison of metabolism of the two compounds in plasma of different species

| Compound name | Plasma source | Highest acetylsalicylic acid concentration in plasma (μg/ml) | Time of highest acetylsalicylic acid concentration in plasma (min) | Highest rate of conversion to acetylsalicylic acid % |
|---|---|---|---|---|
| 2-[2-(acetoxy)benzoyloxy]-N,N-diethylacetamide | human being | 94.68 | 60 min | 52.55 |
| | bama pig | 5.54 | 360 min | 3.08 |
| | rabbit | 4.58 | 60 min | 2.54 |
| | beagle | 1.65 | 60 min | 0.92 |
| | rat | 2.06 | 15 min | 1.14 |
| | mouse | BLOQ | — | — |
| 2-(diethylamino)-ethyl-2-acetoxybenzoate hydrochloride | human being | 9.44 | 60 min | 5.24 |
| | beagle | 2.19 | 60 min | 1.22 |
| | rat | BLOQ | — | — |
| | mouse | BLOQ | — | — |

Note:
BLOQ means below the lower limit of quantification.

In summary, in the plasma of primates (including human beings), the compound represented by Formula (1) of the present disclosure (for example, 2-[2-(acetoxy)benzoyloxy]-N,N-diethylacetamide) is mainly metabolized to acetylsalicylic acid. That is, it is a genuine aspirin prodrug. In contrast, 2-(diethylamino)-ethyl-2-acetoxybenzoate hydrochloride is mainly metabolized to salicylic acid, and thus it can only be regarded as a prodrug of salicylic acid.

Example 4: Inhibitory Effects of 2-[2-(acetoxy) benzoyloxy]-N,N-diethylacetamide and 2-(diethylamino)-ethyl-2-acetoxybenzoate Hydrochloride on Monkey Platelet Aggregation 12 male cynomolgus monkeys were divided into three groups (4 per group), namely a blank group, a 2-(diethylamino)-ethyl-2-acetoxybenzoate hydrochloride treatment group and a 2-[2-(acetoxy)benzoyloxy]-N,N-diethylacetamide treatment group. 2-(diethylamino)-ethyl-2-acetoxybenzoate hydrochloride was dissolved in ddH$_2$O to formulate a 200 mg/ml solution, and 2-[2-(acetoxy)benzoyloxy]-N,N-diethylacetamide was dissolved in a 50% ethanol solution to prepare a 50 mg/ml solution. The dosage for the 2-(diethylamino)-ethyl-2-acetoxybenzoate hydrochloride treatment group was 60 mg/kg, i.e. 0.3 mL/kg; and the dosage for the 2-[2-(acetoxy)benzoyloxy]-N,N-diethylacetamide treatment group was 70 mg/kg, i.e. 1.4 mL/kg. The dose volume for a monkey was calculated based on its weight. The hair on the monkey's back was shaved, and the drug was evenly applied to the bare skin. The drug was administered continuously every day for four weeks. Blank blood was collected before administration, and blood was collected once a week after administration to detect the platelet aggregation ability (the inducer was 1 mM arachidonic acid).

Figure 2:
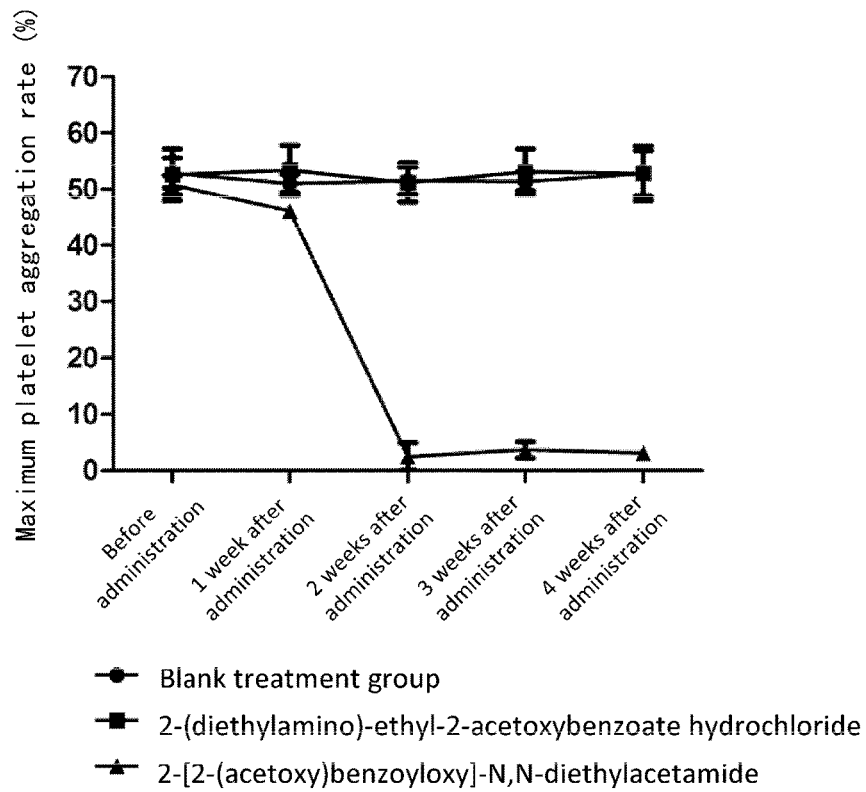
FIG. 2 depicts the inhibitory effect of 2-[2-(acetoxy)benzoyloxy]-N,N-diethylacetamide and 2-(diethylamino)-ethyl-2-acetoxybenzoate hydrochloride on monkey platelet aggregation.

The results of the platelet aggregation ability are shown in FIG. 2. As shown by the results, after the treatment by administration of 2-[2-(acetoxy)benzoyloxy]-N,N-diethylacetamide, the platelet aggregation rate in the blood decreased significantly since the second week, and continued until the end of the experiment, indicating that 2-[2-(acetoxy)benzoyloxy]-N,N-diethylacetamide had a significant inhibitory effect on platelet aggregation after transdermal administration. In contrast, the platelet aggregation rate remained at about 50% after the treatment with 2-(diethylamino)-ethyl-2-acetoxybenzoate hydrochloride, close to that of the blank group, indicating that 2-(diethylamino)-ethyl-2-acetoxybenzoate hydrochloride cannot inhibit platelet aggregation effectively.

These results are consistent with the results of Example 3. In particular, the conversion rate of 2-[2-(acetoxy)benzoyloxy]-N,N-diethylacetamide into acetylsalicylic acid in monkey plasma was as high as 78.72%. The ester group in this compound is preferentially hydrolyzed in the plasma to generate acetylsalicylic acid, and then the acetyl group is removed so that this compound is metabolized to salicylic acid. This process is consistent with the metabolic order of acetylsalicylic acid (so this compound is a genuine acetylsalicylic acid prodrug). Therefore, this compound can inhibit platelet aggregation effectively. In contrast, the acetyl group in 2-(diethylamino)-ethyl-2-acetoxybenzoate hydrochloride is preferentially hydrolyzed in plasma (to the extent that a salicylic acid prodrug is formed), and then the transdermal group is removed so that this compound is metabolized to salicylic acid. Therefore, this compound has no anti-platelet aggregation effect (salicylic acid has no anti-platelet aggregation effect).

Example 5: X-Ray Powder Diffraction Measurement of 2-[2-(acetoxy)benzoyloxy]-N,N-diethylacetamide Crystals The crystal of 2-[2-(acetoxy)benzoyloxy]-N,N-diethylacetamide obtained in Example 1 was subjected to X-ray powder diffraction. The detection instrument used was: Panalytical X' Pert Powder powder X-ray diffractometer; measurement conditions: Cu-Kα; tube pressure/tube current: 40 kV/40 mA; scanning angle: 3.0131°-59.9791°; scanning step length: 0.0260°; emission slit: 0.2177; test temperature: 25° C. The data obtained are shown in Table 5.

TABLE 5

| Pos.[° 2θ] | Height[cts] | FWHM[° 2θ] | d-spacing (Å) | Rel.Int.[%] |
|---|---|---|---|---|
| 9.4285 | 17225.46 | 0.1535 | 9.38031 | 28.47 |
| 10.3500 | 32604.38 | 0.0768 | 8.54712 | 53.89 |
| 10.5385 | 60506.98 | 0.1279 | 8.39469 | 100.00 |
| 12.1604 | 1035.88 | 0.2303 | 7.27845 | 1.71 |
| 16.3274 | 15831.89 | 0.2814 | 5.42907 | 26.17 |
| 18.0996 | 1662.92 | 0.1279 | 4.90129 | 2.75 |
| 18.9160 | 2680.04 | 0.1279 | 4.69155 | 4.43 |
| 20.4592 | 4480.91 | 0.2558 | 4.34103 | 7.41 |
| 21.1665 | 9725.47 | 0.3070 | 4.19755 | 16.07 |
| 21.8043 | 3681.10 | 0.2047 | 4.07618 | 6.08 |
| 22.6957 | 6511.42 | 0.2814 | 3.91806 | 10.76 |
| 24.4651 | 7127.69 | 0.2558 | 3.63855 | 11.78 |
| 25.8128 | 782.22 | 0.2047 | 3.45156 | 1.29 |
| 26.3216 | 868.02 | 0.1279 | 3.38598 | 1.43 |
| 26.9904 | 260.08 | 0.2558 | 3.30359 | 0.43 |
| 27.8508 | 2767.57 | 0.1791 | 3.20345 | 4.57 |
| 28.4536 | 2028.19 | 0.2047 | 3.13694 | 3.35 |
| 28.8459 | 1793.03 | 0.1535 | 3.09516 | 2.96 |
| 29.4468 | 1232.99 | 0.1279 | 3.03336 | 2.04 |
| 29.9437 | 1803.11 | 0.2303 | 2.98414 | 2.98 |
| 30.5841 | 1067.44 | 0.1535 | 2.92310 | 1.76 |
| 31.9930 | 1494.15 | 0.1535 | 2.79752 | 2.47 |
| 32.9487 | 1265.64 | 0.2558 | 2.71853 | 2.09 |
| 33.4855 | 269.87 | 0.2047 | 2.67617 | 0.45 |
| 34.3099 | 678.87 | 0.2047 | 2.61373 | 1.12 |
| 34.7802 | 513.41 | 0.1535 | 2.57945 | 0.85 |
| 35.3430 | 888.84 | 0.2303 | 2.53966 | 1.47 |
| 35.8309 | 204.07 | 0.1535 | 2.50619 | 0.34 |
| 36.6231 | 337.57 | 0.2558 | 2.45378 | 0.56 |
| 37.8715 | 1335.48 | 0.1791 | 2.37571 | 2.21 |
| 38.3421 | 559.20 | 0.2303 | 2.34763 | 0.92 |
| 39.0142 | 714.86 | 0.2558 | 2.30872 | 1.18 |
| 39.9471 | 223.26 | 0.3070 | 2.25693 | 0.37 |
| 40.4205 | 182.15 | 0.2047 | 2.23159 | 0.30 |
| 41.2068 | 542.80 | 0.2047 | 2.19080 | 0.90 |
| 41.5095 | 675.49 | 0.2047 | 2.17552 | 1.12 |
| 43.2239 | 144.41 | 0.6140 | 2.09313 | 0.24 |
| 45.6460 | 248.96 | 0.2558 | 1.98754 | 0.41 |
| 47.2626 | 342.29 | 0.2558 | 1.92326 | 0.57 |
| 49.3698 | 144.98 | 0.2047 | 1.84599 | 0.24 |
| 50.3891 | 296.83 | 0.2047 | 1.81101 | 0.49 |
| 52.0256 | 139.88 | 0.4093 | 1.75784 | 0.23 |
| 52.9649 | 67.86 | 0.3070 | 1.72885 | 0.11 |
| 56.3879 | 62.58 | 0.3070 | 1.63176 | 0.10 |
| 57.6414 | 60.55 | 0.7488 | 1.59790 | 0.10 |

Figure 3:
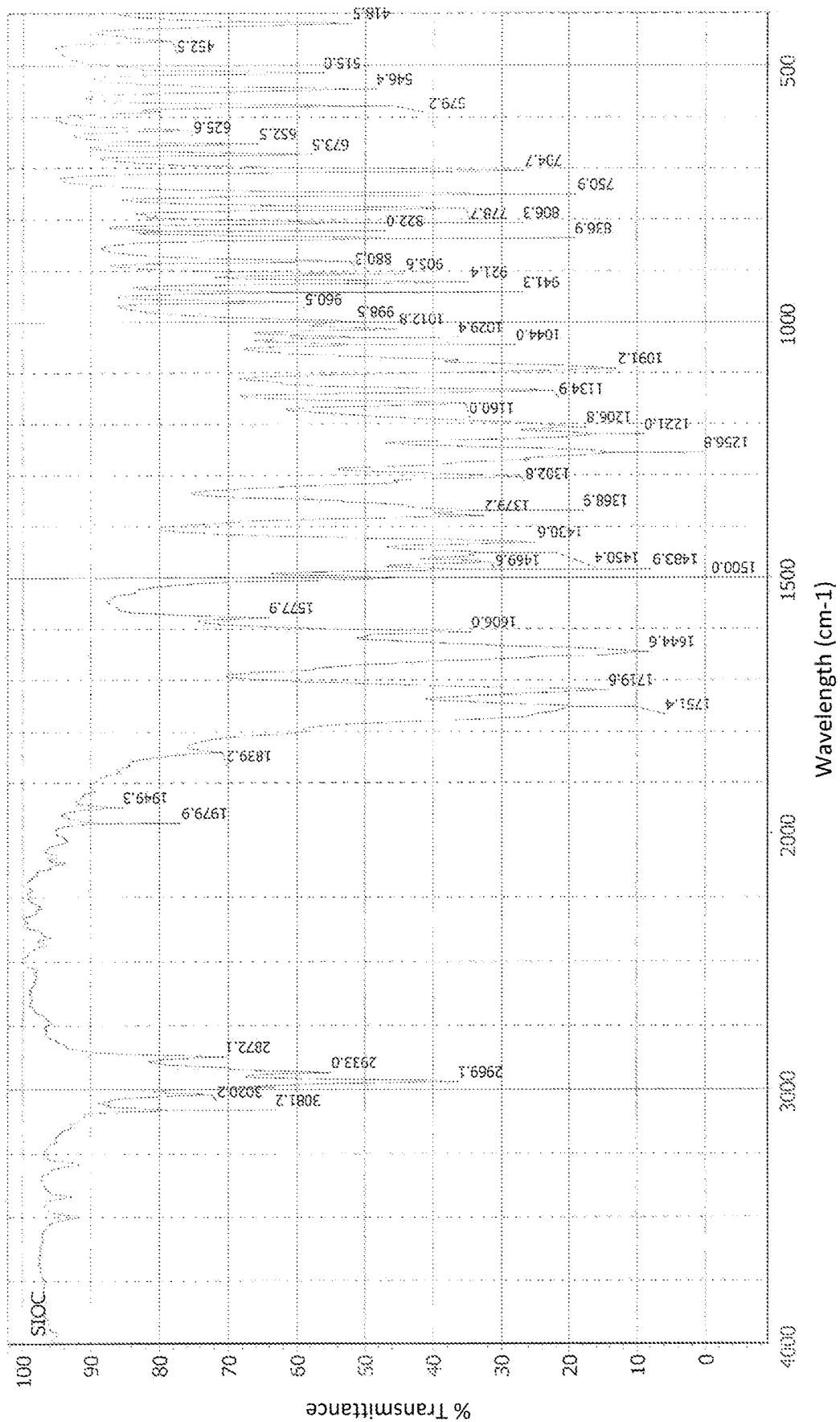
FIG. 3 depicts the infrared absorption spectrum of a crystal of 2-[2-(acetoxy)benzoyloxy]-N,N-diethylacetamide.

Example 6: Infrared Absorption Spectrometry of a Crystal of 2-[2-(acetoxy)benzoyloxy]-N,N-diethylacetamide The crystal of 2-[2-(acetoxy)benzoyloxy]-N,N-diethylacetamide obtained in Example 1 was subjected to infrared absorption spectrometry using Nicolet iZ10 Fourier Transform Infrared Spectrometer. A potassium bromide tableting method was utilized. Number of sample scanning: 32; number of background scanning: 32; resolution: 4.000; sampling gain: 1.0; moving mirror speed: 0.4747; diaphragm: 150.00. The resulting infrared absorption spectrum is shown in FIG. 3.

Example 7: Study on Stability of a Crystal of 2-[2-(acetoxy)benzoyloxy]-N,N-diethylacetamide The crystal of 2-[2-(acetoxy)benzoyloxy]-N,N-diethylacetamide obtained in Example 1 was placed at 25° C.±2° C., and sampled at the time of 0 month, 3 months, 6 months, 9 months, 12 months to determine the impurities and assay thereof. The impurities and assay were determined by HPLC (external standard method). As shown by the results, the crystal of the present disclosure was very stable after stored at 25° C.±2° C. for 12 months. The detailed data were shown in Table 6.

The conditions for the HPLC determination are as follows:
Column: Inertsil ODS C18, 4.6×250 mm, 5 μm
Detection wavelength: 276 nm, 303 nm
Column temperature: 33° C.
Flow rate: 1.0 mL/min
Injection volume: 10 μL
Mobile phase: 0.1% tetrahydrofuran aqueous solution: acetonitrile=55:45
Running time: 15 min

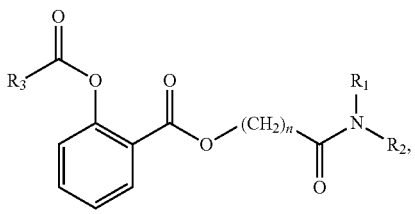

(1)

wherein $R_1$ and $R_2$ each independently represent H, unsubstituted $C_1$-$C_{30}$ alkyl, unsubstituted alkoxy, unsubstituted $C_2$-$C_{30}$ alkenyl, unsubstituted $C_6$-$C_{30}$ aryl, unsubstituted $C_7$-$C_{30}$ aralkyl, or unsubstituted $C_3$-$C_{30}$ cycloalkyl, or $R_1$ and $R_2$ form 4-, 5-, 6- or 7-membered heterocycle, together with the N to which they are linked;

$R_3$ represents unsubstituted $C_1$-$C_{12}$ alkyl;

n is 1; and a crystal of the compound represented by Formula (1) comprises characteristic peaks in an X-ray powder diffraction (XRPD) pattern at the following 2θ angles: 9.4°±0.2°, 10.3°±0.2°, 12.2°±0.2°, 18.1°±0.2°, 21.8°±0.2°, 24.4°±0.2°, 29.4°±0.2°, 30.6°±0.2°, 31.9°±0.2°, 36.6°±0.2°,

TABLE 6

Stability data of a crystal of 2-[2-(acetoxy)benzoyloxy]-N,N-diethylacetamide

| | Test Items | Month 0 | Month 3 | Month 6 | Month 9 | Month 12 |
|---|---|---|---|---|---|---|
| Impurities | 2-(diethylamino)-2-oxoethyl-2-salicylate hydrochloride | 0.35% | 0.42% | 0.39% | 0.45% | 0.46% |
| | acetylsalicylic acid | 0.0063% | 0.0059% | 0.0062% | 0.0061% | 0.0066% |
| | salicylic acid | 0.00134% | 0.00148% | 0.00139% | 0.00112% | 0.00124% |
| | Unspecified impurities | not detected | not detected | not detected | not detected | not detected |
| | Assay | 99.63% | 99.58% | 99.64% | 99.66% | 99.58% |

Although the present disclosure has described specific examples, it is obvious to those skilled in the art that various changes and modifications can be made to the present disclosure without departing from the spirit and scope of the present disclosure. Therefore, the appended claims cover all these changes within the scope of the present disclosure.

What is claimed is:

1. A crystal of 2-[2-(acetoxy)benzoyloxy]-N,N-diethylacetamide, wherein the crystal comprises characteristic peaks in an X-ray powder diffraction (XRPD) pattern at the following 2θ angles: 9.4°±0.2°, 10.3°±0.2°, 12.2°±0.2°, 18.1°±0.2°, 21.8°±0.2°, 24.4°±0.2°, 29.4°±0.2°, 30.6°±0.2°, 31.9°±0.2°, 36.6°±0.2°.

2. The crystal according to claim 1, wherein the crystal further comprises characteristic peaks in an X-ray powder diffraction (XRPD) pattern at the following 2θ angles: 20.4°±0.2°, 25.8°±0.2°, 27.0°±0.2°, 28.4°±0.2°, 28.8°±0.2°, 32.9°±0.2°.

3. A pharmaceutical composition as a transdermal dosage form or a transmucosal dosage form, comprising a therapeutically effective amount of the compound represented by Formula (1):

or the pharmaceutically acceptable salt thereof, and a pharmaceutically acceptable carrier.

4. The pharmaceutical composition of claim 3, wherein the dosage form is selected from the group consisting of patch, suppository, drop, liniment, gel, ointment, spray, aerosol, and powder.

5. The pharmaceutical composition according to claim 3, wherein the pharmaceutical composition is used to treat acetylsalicylic acid indications or treat anti-platelet aggregation.

6. The pharmaceutical composition according to claim 5, wherein the acetylsalicylic acid indications include pain, fever, rheumatism, arthritis, diabetes or its complications, dementia, cardiovascular diseases, and cerebrovascular diseases.

7. A method of treating acetylsalicylic acid indications or anti-platelet aggregation, comprising the step of applying the compound represented by Formula (1) or the pharmaceutically acceptable salt in a transdermal dosage form or a transmucosal dosage form to a subject to be treated:

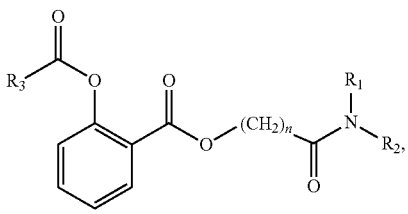

(1)

wherein $R_1$ and $R_2$ each independently represent H, unsubstituted $C_1$-$C_{30}$ alkyl, unsubstituted alkoxy, unsubstituted $C_2$-$C_{30}$ alkenyl, unsubstituted $C_6$-$C_{30}$ aryl, unsubstituted $C_7$-$C_{30}$ aralkyl, or unsubstituted $C_3$-$C_{30}$ cycloalkyl, or $R_1$ and $R_2$ form 4-, 5-, 6- or 7-membered heterocycle, together with the N to which they are linked;

$R_3$ represents unsubstituted $C_1$-$C_{12}$ alkyl;

n is 1; and a crystal of the compound represented by Formula (1) comprises characteristic peaks in an X-ray powder diffraction (XRPD) pattern at the following 2θ angles: 9.4°±0.2°, 10.3°±0.2°, 12.2°±0.2°, 18.1°±0.2°, 21.8°±0.2°, 24.4°±0.2°, 29.4°±0.2°, 30.6°±0.2°, 31.9°±0.2°, 36.6°±0.2°.

8. The method according to claim 7, wherein the transdermal dosage form or the transmucosal dosage form is selected from the group consisting of patch, suppository, drop, liniment, gel, ointment, spray, aerosol, and powder.

9. The method according to claim 7, wherein the acetylsalicylic acid indications include pain, fever, rheumatism, arthritis, diabetes or its complications, dementia, cardiovascular diseases, and cerebrovascular diseases.

10. The method according to claim 7, wherein the subject to be treated is a primate.

11. The method according to claim 10, wherein the primate is a monkey or a human being.

12. The pharmaceutical composition according to claim 3, wherein $R_1$ and $R_2$ each independently represent unsubstituted $C_1$-$C_6$ alkyl, unsubstituted $C_1$-$C_6$ alkoxy, or unsubstituted $C_2$-$C_6$ alkenyl.

13. The pharmaceutical composition according to claim 3, wherein $R_1$ and $R_2$ each independently represent methyl or ethyl.

14. The pharmaceutical composition according to claim 3, wherein $R_3$ represents unsubstituted $C_1$-$C_6$ alkyl.

15. The pharmaceutical composition according to claim 3, wherein $R_3$ represents methyl.

16. The pharmaceutical composition according to claim 3, wherein the compound represented by Formula (1) is selected from the group consisting of: 2-[2-(acetoxy)benzoyloxy]-N,N-diethylacetamide, 2 [2 (acetoxy)benzoyloxy]-N-ethylacetamide, 2-[2-(acetoxy)benzoyloxy]-N-methylacetamide, 2-[2-(acetoxy)benzoyloxy]-acetylcycloethylamine, 2-[2-(acetoxy)benzoyloxy]-acetylpiperidine, 3-[2-(acetoxy)benzoyloxy]-N,N-diethylpropionamide, 3-[2-(acetoxy)benzoyloxy]-N,N-dimethylpropionamide, 4-[2-(acetoxy)benzoyloxy]-N,N-diethylbutanamide, 4-[2-(acetoxy)benzoyloxy]-N,N-dimethylbutanamide, 5-[2-(acetoxy)benzoyloxy]-N,N-dimethylvaleramide, and 5-[2-(acetoxy)benzoyloxy]-N,N-dimethylvaleramide.

17. The pharmaceutical composition according to claim 3, wherein the compound represented by Formula (1) is a crystal of 2-[2-(acetoxy)benzoyloxy]-N,N-diethylacetamide that comprises characteristic peaks in an X-ray powder diffraction (XRPD) pattern at the following 2θ angles: 9.4°±0.2°, 10.3°±0.2°, 12.2°±0.2°, 18.1°±0.2°, 21.8°±0.2°, 24.4°±0.2°, 29.4°±0.2°, 30.6°±0.2°, 31.9°±0.2°, 36.6°±0.2°.

18. The pharmaceutical composition according to claim 17, wherein the crystal further comprises characteristic peaks in an X-ray powder diffraction (XRPD) pattern at the following 2θ angles: 20.4°±0.2°, 25.8°±0.2°, 27.0°±0.2°, 28.4°±0.2°, 28.8°±0.2°, 32.9°±0.2°.

19. The method according to claim 7, wherein the compound represented by Formula (1) is a crystal of 2-[2-(acetoxy)benzoyloxy]-N,N-diethylacetamide that comprises characteristic peaks in an X-ray powder diffraction (XRPD) pattern at the following 2θ angles: 9.4°±0.2°, 10.3°±0.2°, 12.2°±0.2°, 18.1°±0.2°, 21.8°±0.2°, 24.4°±0.2°, 29.4°±0.2°, 30.6°±0.2°, 31.9°±0.2°, 36.6°±0.2°.

20. The method according to claim 19, wherein the crystal further comprises characteristic peaks in an X-ray powder diffraction (XRPD) pattern at the following 2θ angles: 20.4°±0.2°, 25.8°±0.2°, 27.0°±0.2°, 28.4°±0.2°, 28.8°±0.2°, 32.9°±0.2°.

21. The method according to claim 7, wherein $R_1$ and $R_2$ each independently represent unsubstituted $C_1$-$C_6$ alkyl, unsubstituted $C_1$-$C_6$ alkoxy, or unsubstituted $C_2$-$C_6$ alkenyl.

22. The method according to claim 7, wherein $R_1$ and $R_2$ each independently represent methyl or ethyl.

23. The method according to claim 7, wherein $R_3$ represents unsubstituted $C_1$-$C_6$ alkyl.

24. The method according to claim 7, wherein $R_3$ represents methyl.

25. The method according to claim 7, wherein the compound represented by Formula (1) is selected from the group consisting of: 2-[2-(acetoxy)benzoyloxy]-N,N-diethylacetamide, 2 [2 (acetoxy)benzoyloxy]-N-ethyl acetamide, 2[2-(acetoxy)benzoyl oxy]-N-methyl acetamide, 2-[2-(acetoxy) benzoyloxy]-acetylcyclethylamine, 2-[2-(acetoxy) benzoyloxy]-acetyl piperidine, 3-[2-(acetoxy)benzoyloxy]-N,N-di ethyl propionamide, 3-[2-(acetoxy)benzoyloxy]-N,N-di methyl propionamide, 4-[2-(acetoxy)benzoyloxy]-N,N-diethylbutanamide, 4-[2-(acetoxy)benzoyloxy]-N,N-dimethylbutanamide, 5-[2-(acetoxy)benzoyloxy]-N,N-dimethylvaleramide, and 5-[2-(acetoxy)benzoyloxy]-N,N-dimethylvaleramide.

* * * * *